United States Patent [19]
Kirsch et al.

[11] Patent Number: 5,976,161
[45] Date of Patent: Nov. 2, 1999

[54] TISSUE EVERTING APPARATUS AND METHOD

[75] Inventors: Wolff M. Kirsch; Yong Hua Zhu, both of Redlands, Calif.; Robert B. Cushman, Cedar Crest, N.Mex.; Ellen Golds, Hastings-on-Hudson, N.Y.; H. Jonathan Tovey, Bethel, Conn.

[73] Assignee: University of New Mexico, Albuquerque, N.Mex.

[21] Appl. No.: 09/003,761

[22] Filed: Jan. 7, 1998

[51] Int. Cl.$^6$ ............................ A61B 17/00; A61B 17/28
[52] U.S. Cl. ............................................ 606/149; 606/205
[58] Field of Search ................................ 606/139, 149, 606/205–208, 209

[56] References Cited

U.S. PATENT DOCUMENTS

| | | |
|---|---|---|
| 3,040,748 | 6/1962 | Klein et al. . |
| 4,470,415 | 9/1984 | Wozniak . |
| 4,622,970 | 11/1986 | Wozniak . |
| 4,950,281 | 8/1990 | Kirsch et al. . |
| 5,238,002 | 8/1993 | Devlin et al. ............................ 606/205 |
| 5,300,065 | 4/1994 | Anderson . |
| 5,472,439 | 12/1995 | Hurd ........................................ 606/205 |
| 5,486,187 | 1/1996 | Schenck . |
| 5,520,704 | 5/1996 | Castro et al. . |
| 5,527,324 | 6/1996 | Krantz et al. . |
| 5,535,754 | 7/1996 | Doherty ............................... 606/205 X |
| 5,573,546 | 11/1996 | Nakao ................................. 606/205 X |

*Primary Examiner*—Michael Buiz
*Assistant Examiner*—Vikki Trinh

[57] ABSTRACT

A tissue everting apparatus includes at least one elongated frame, at least one actuator slidably mounted to the frame and longitudinally movable between proximal and distal positions, a tissue everting bulbous tip, and at least two prongs which are laterally movable between open and closed positions. The bulbous tissue everting tip is positioned, for example, in the lumen of a vascular segment to evert the edge and the prong is closed to capture the everted edge of the vascular segment. The edge of a second vascular segment is everted and captured in a similar manner with the edges being brought together to form a flange-like structure to which one or more surgical clips may be applied to fasten the segments together.

11 Claims, 15 Drawing Sheets

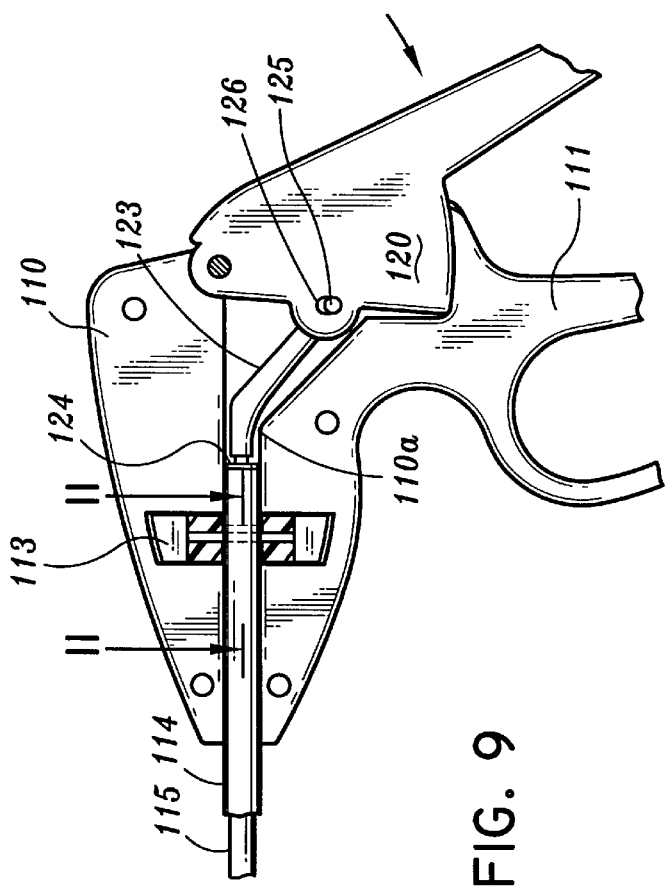
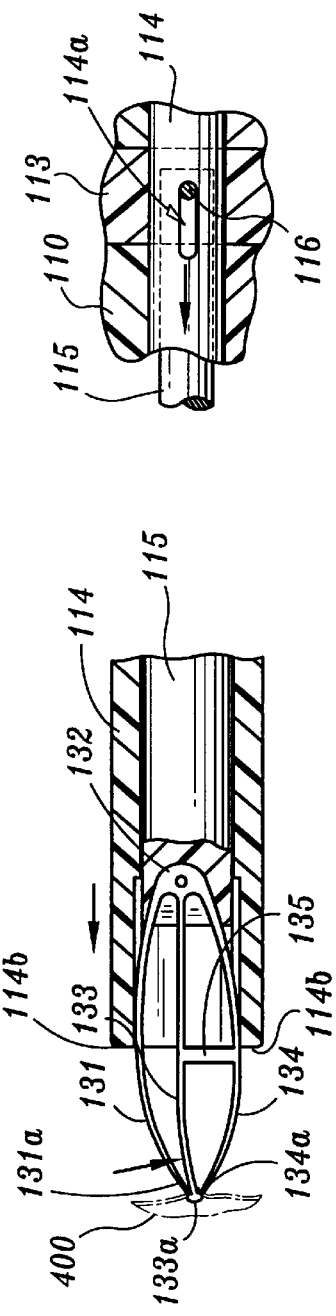
FIG. 9
FIG. 11
FIG. 10

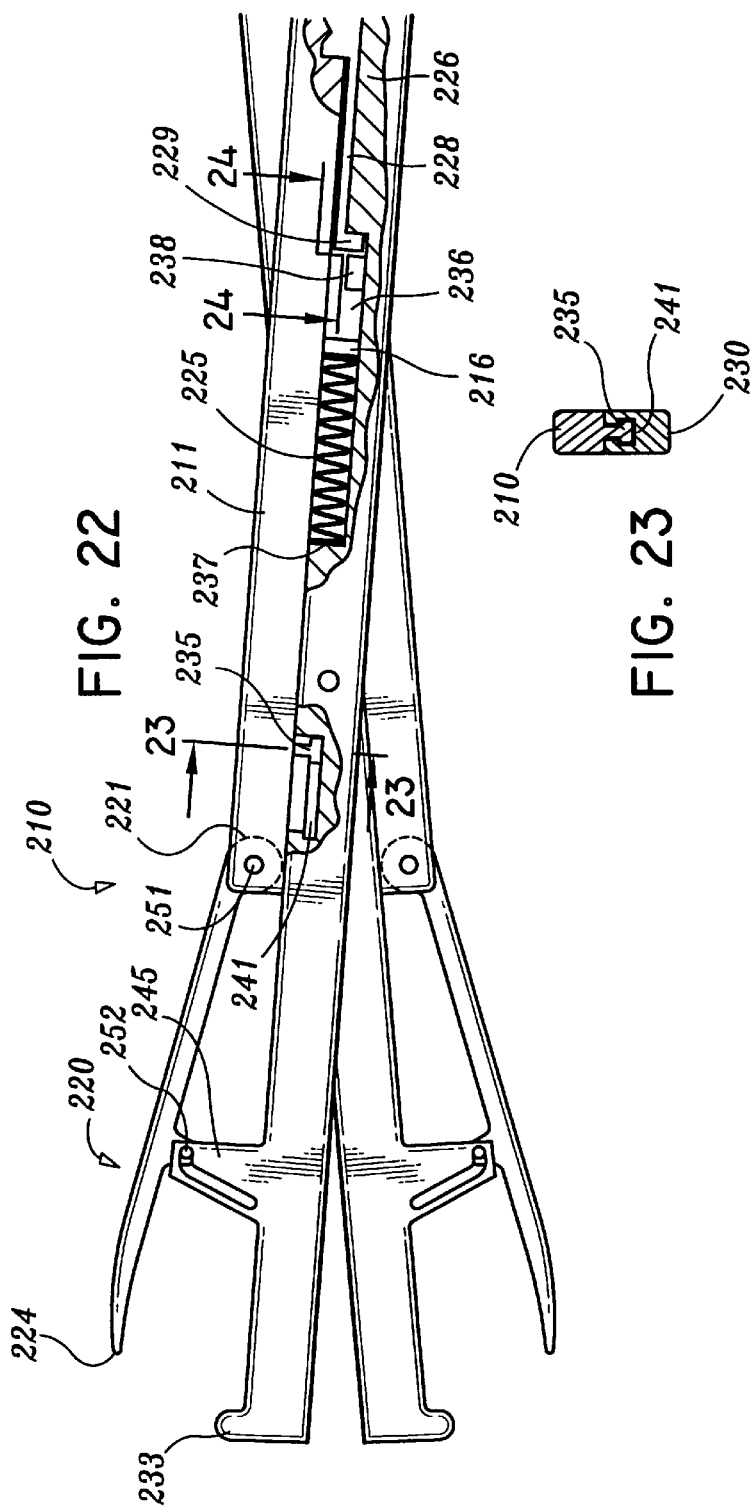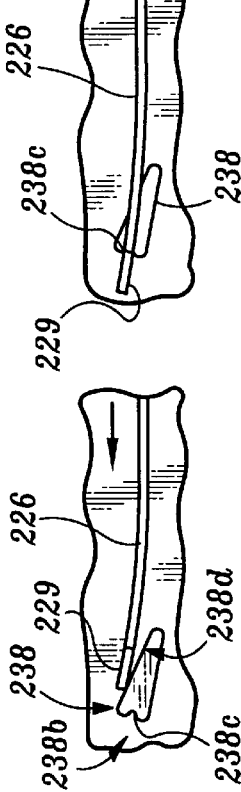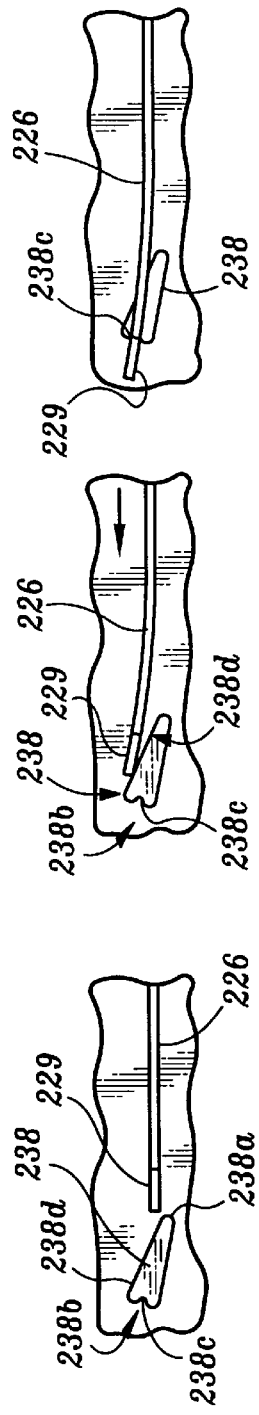

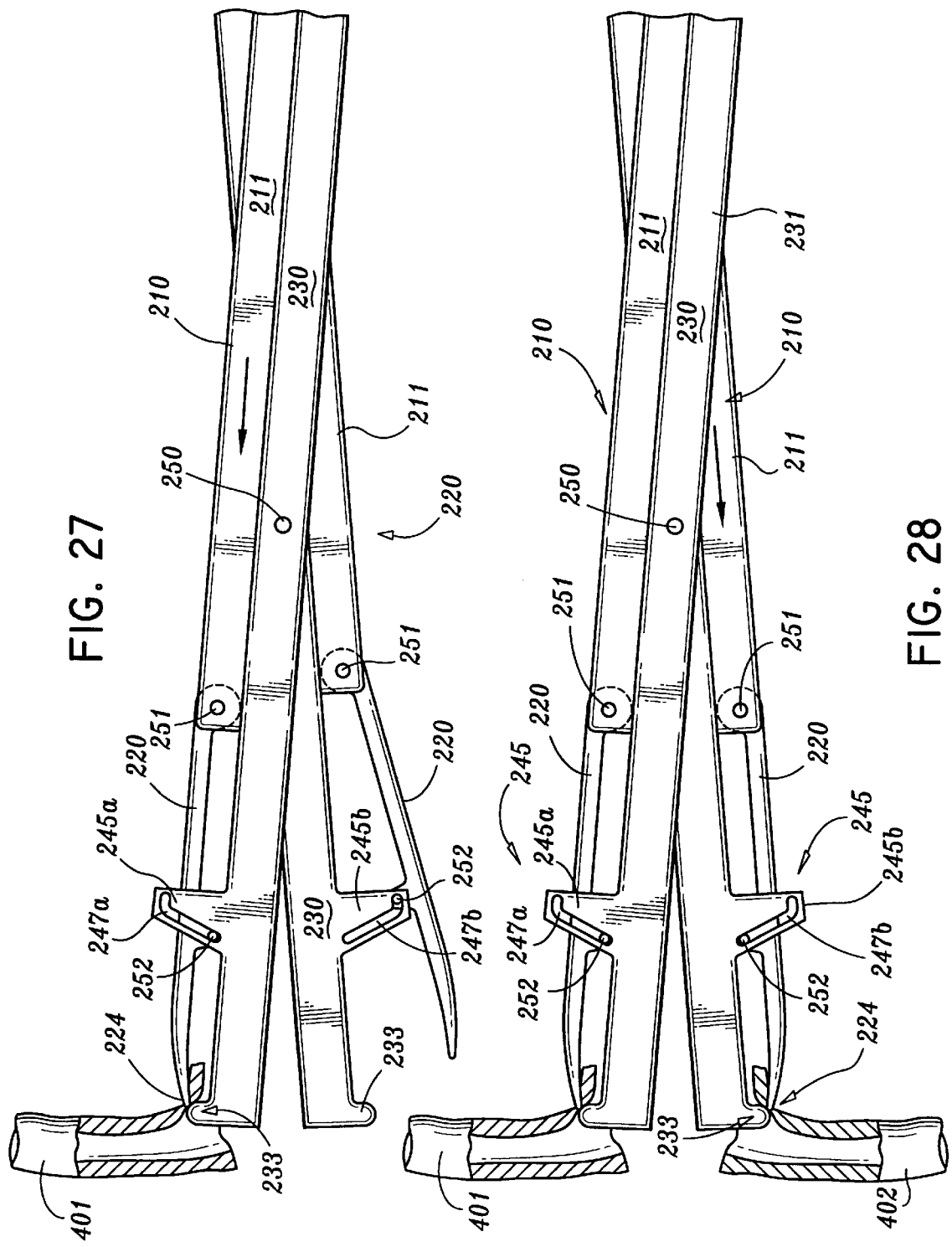

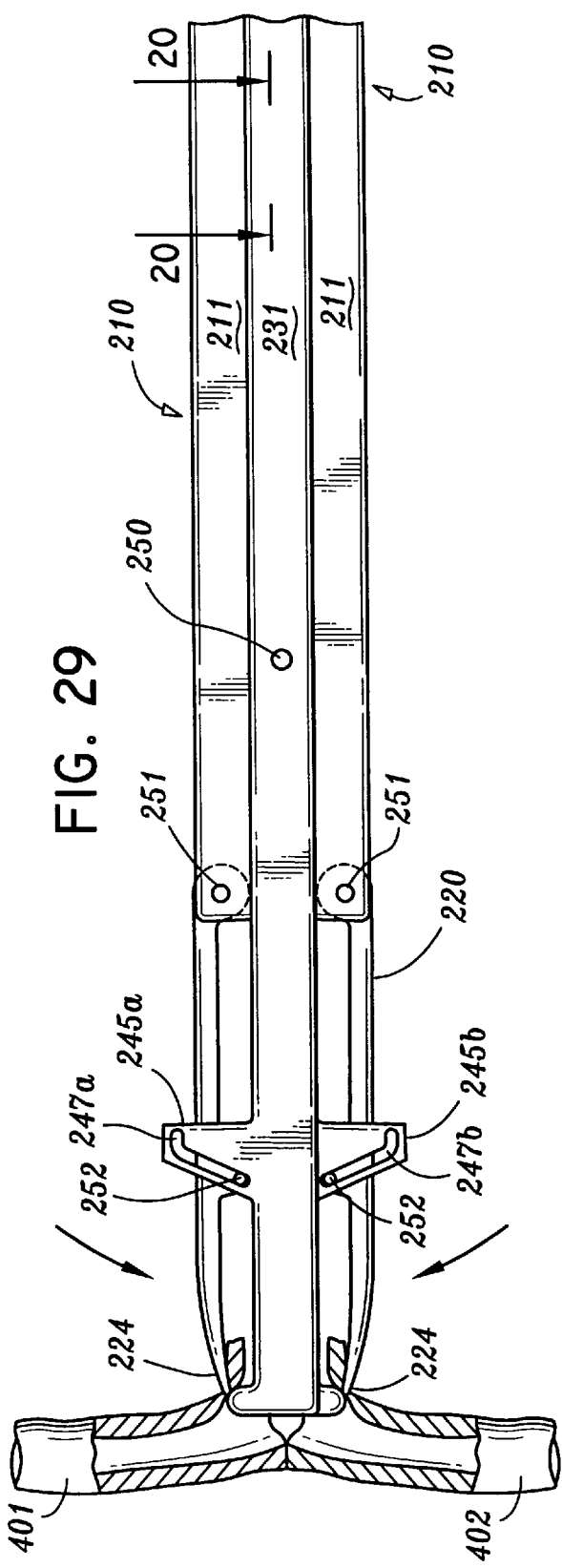
FIG. 29
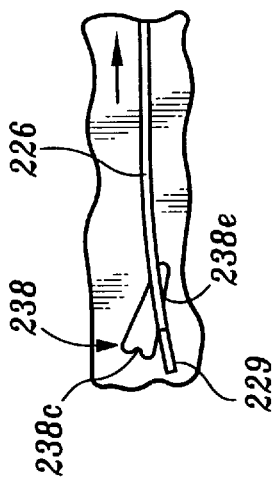
FIG. 32
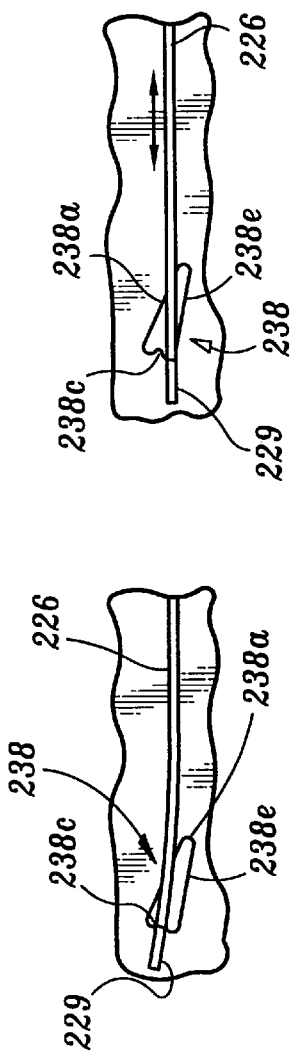
FIG. 31
FIG. 30

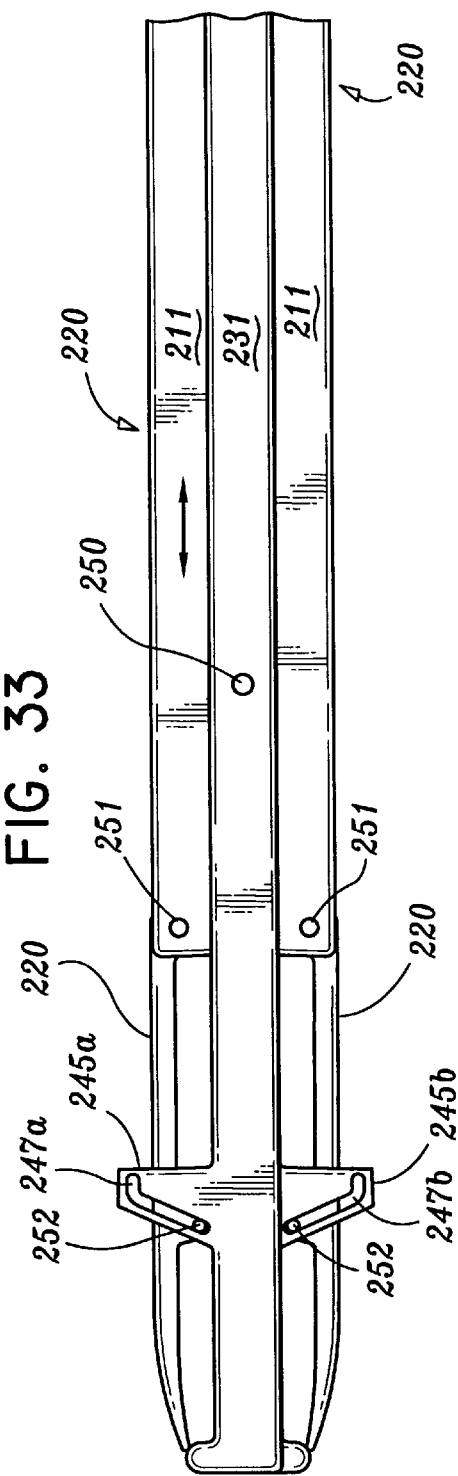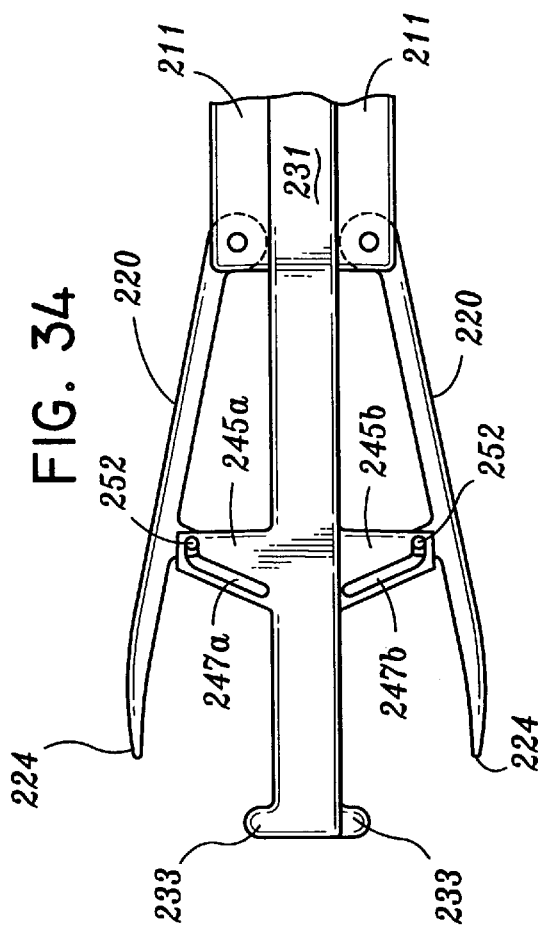

TISSUE EVERTING APPARATUS AND METHOD

BACKGROUND

1. Technical Field

The disclosure herein relates to surgical instrumentation for everting body tissue, particularly blood vessels, in minimally invasive or open surgery, and methods for using same.

2. Background of the Art

In surgical procedures for edge to edge joining of body tissue, the edges of the tissue are often everted and held in close approximation in order for the tissue to be sutured. For example, to join the ends of tubular structures such as blood vessels, the ends of the blood vessels can be everted to facilitate joining by suture threads and more recently by clips. Other methods of joining such as side-to-side and end-to-side can also be used for joining tubular structures. A preferable way to join body tissue is by the application of non-tissue penetrating clips, which cause less trauma to the body tissue than suturing or penetrating clips. Such clips require proper eversion of the body tissue.

Everting instruments are known in the art. For example, U.S. Pat. No. 5,300,065 to Anderson discloses a method and apparatus for holding and sealing a longitudinally extending edge of tissue. The tissue is everted and held in position by a clamping member.

U.S. Pat. No. 5,527,324 to Krantz et al. discloses a surgical stent for use in supporting the walls of a tubular organ during anastomosis. The stent includes a circumferential ridge adapted to evert the edges of the tubular organ to facilitate suturing.

U.S. Pat. No. 4,622,970 to Wozniak discloses a vascular everting instrument having an annular member with an iris-diaphragm mechanism to flare the leading edge of the blood vessel to facilitate anastomosis.

U.S. Pat. No. 5,486,187 to Schenck discloses a method and device for anastomosis of blood vessels. The device includes a ring-like member through which the end of a first vessel is extended and everted back over. A second vessel end is drawn over the everted first vessel end to place the lumen of these vessels in apposition. Fasteners are then applied to clinch the vessels.

U.S. Pat. No. 5,520,704 to Castro et al. and U.S. Pat. No. 4,950,281 to Kirsch et al. disclose everting forceps which include first and second outer resilient legs interconnected at one end, and a third leg intermediate the pair of outer legs. The outer legs terminate at tips provided with arcuate jaws. The intermediate leg terminates in a spherical tip.

What is needed is improved instrumentation for everting vessels.

What is also needed is improved instrumentation which can be used in minimally invasive surgical procedures such as laparoscopic or endoscopic procedures. Typically, in minimally invasive procedures a cannula is placed in an opening in a wall of body tissue and the surgical instrumentation is sent through the cannula into the patient's body wherein the operation is performed. One or more additional cannulas provide access for fiberoptic viewing instruments and other surgical instrumentation. The operating end portion of the instruments is generally long and narrow to be able to fit through the cannula and reach the inside of the body cavity where the operation is being performed. In procedures such as abdominal surgery wherein the operating site is insufflated, it is generally necessary to have a seal both within the equipment and between the equipment and cannula to prevent the entry or egress of gases or other fluids into or out from the patient's body. An advantage of minimally invasive surgery is that there is much less trauma to the patient. Both operating time and recovery time are significantly shortened.

SUMMARY

An apparatus is provided for everting body tissue. The apparatus includes a handle portion, an endoscopic portion extending therefrom and including an actuator; longitudinally movable between a first position and a second position; a tissue everting tip; and first and second prongs, extending distally from the endoscopic portion and being relatively movable with respect to each other in at least a partly lateral direction between a laterally open position and a closed tissue-capturing position in response to the longitudinal movement of the actuator between first and second positions.

In one embodiment, the actuator is a tubular member having a bore through which the elongated frame is disposed. The apparatus can include a third prong, all of the prongs being connected at a proximal base portion, which is fixedly connected to a distal end of the elongated frame. The prongs and base may form a single piece grasper fabricated from resilient material such as synthetic polymer, stainless steel or titanium. The third prong is connected to the second prong by a laterally extending reinforcement strip spaced apart from the base, the third prong extending distally and rectilinearly from the base of the grasper, and the first and second prongs extending arcuately from the base of the grasper. The first, second, and third prongs each have a distal end, with the tissue everting tip being a bulbous portion positioned at the distal end of the third prong and being biased to the distal end of the second prong in response to movement of the actuator from the proximal first position to the distal second position and in response to movement of the first prong to the closed tissue-capturing position.

In another embodiment, the first, second, and third prongs each have a distal end, with the tissue everting tip being a bulbous portion positioned at the distal end of the third prong, the distal ends of the first and second prongs being biased towards the tissue everting tip in response to movement of the actuator from the proximal first position to the distal second position. The distal ends of the first and second prongs are sequentially biased in response to contact by an annular distal edge of the actuator by, for example, use of unequally spaced camming projections on the first and second prongs, or an angled distal edge of the actuator.

Yet another embodiment includes first and second elongated members movably mounted to each other and having tissue everting portions, and first and second prongs terminating in distal tips. The tissue everting portions are preferably bulbous portions positioned at the distal end portion of each of the first and second members.

Also provided herein is a method for using the apparatus described herein in a surgical procedure for everting and fastening the end segments of body tissue.

BRIEF DESCRIPTION OF THE DRAWINGS

Various embodiments are described herein with reference to the drawings wherein:

FIG. 9 is a cut-away partly sectional side elevational view of the handle portion of the apparatus in a fully actuated condition;

FIG. 10 is a sectional side elevational view of the grasper at the distal end of the apparatus in a fully actuated condition;

FIG. 11 is a sectional view of the connection between the rotating knob and the outer tube and inner shaft in a fully actuated condition;

FIG. 22 is a partly cutaway sectional side view of the embodiment of FIG. 19;

FIG. 23 is a sectional view taken along line 23—23 in FIG. 22;

FIG. 24 is a top view taken along line 24—24 of FIG. 22;

FIGS. 25 to 26 are top views sequentially illustrating the interaction of the leaf spring and baffle during actuation of the apparatus;

FIGS. 27 and 28 are side views sequentially illustrating the closing of the jaws to capture everted tissue;

FIG. 29 is a side view illustrating the scissor like action of the apparatus to bring everted and captured ends of body tissue into juxtaposition;

FIGS. 30 to 32 are top views sequentially illustrating the interaction of the leaf spring and baffle during release of the tissue and opening of the jaws; and FIGS. 33 and 34 are side views illustrating opening of the jaws.

DETAILED DESCRIPTION OF PREFERRED EMBODIMENT(S)

Figure 1:
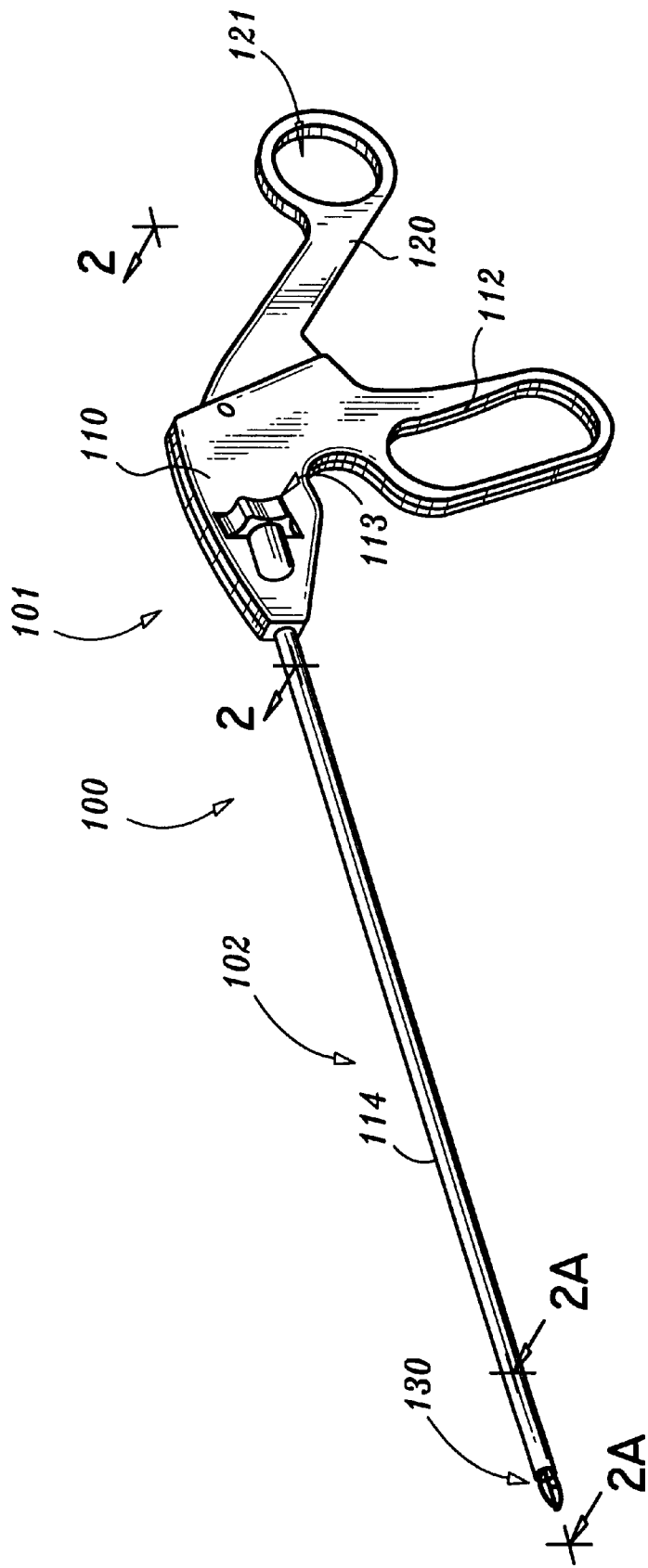
FIG. 1 is a perspective view of a first embodiment of the endoscopic tissue everting apparatus.

Referring now to FIG. 1, an endoscopic everting instrument 100 is shown which comprises a handle portion 101 and an elongated endoscopic portion 102.

The handle portion 101 includes a body 110, a finger grip 112, a rotator knob 113, and a trigger 120 having a finger ring 121.

The endoscopic portion 102 includes an outer tube 114 and a shaft 115 disposed within the bore of outer tube 114. (See, FIG. 3) Affixed to the distal end of shaft 115 is a tissue grasper 130.

Figure 2:
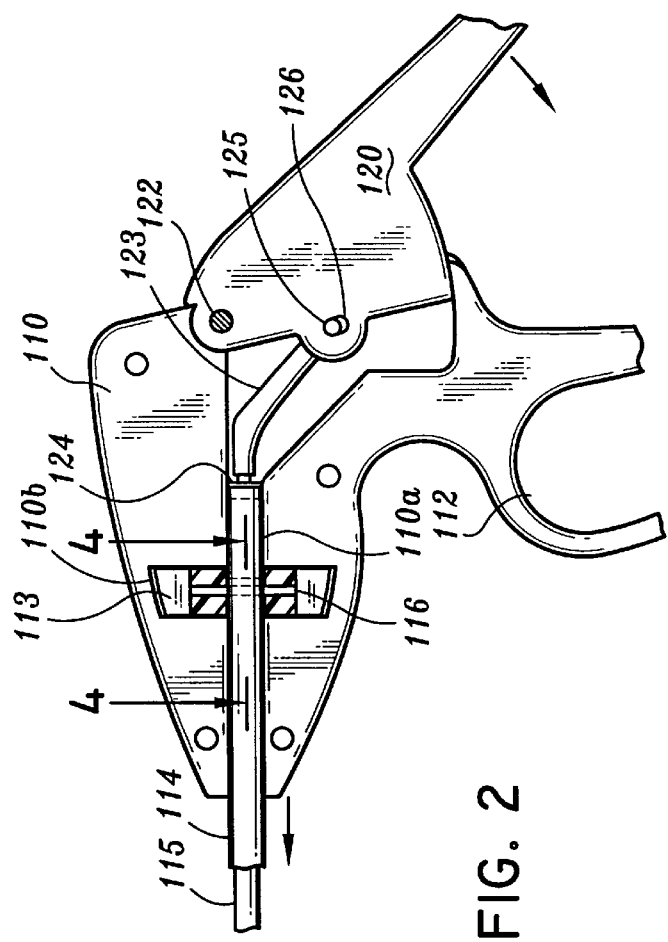
FIG. 2 is a partly sectional cut-away side elevational view of the handle portion of the apparatus in unactuated condition.

Referring also now to FIG. 2, the body 110 includes a bore 110a in which the outer tube 114 and shaft 115 are disposed. Trigger 120 is pivotably mounted to the body by means of pivot pin 122, and is connected to link 123 by transversely oriented pin 125. Pin 125 is fixedly attached to link 123 and is disposed through slot 126 in the trigger. Slot 126 is configured and dimensioned so as to accommodate the lost motion of pin 125 relative to slot 126 as the trigger 120 is pivoted. Link 123 is fixedly attached to connector 124, which is attached to the proximal end of the outer tube 114. Thus, when the trigger 120 is actuated by user applied pressure it rotates clockwise (as shown) around pivot pin 122 and, via link 123, moves the outer tube 114 distally forward.

Figure 4:
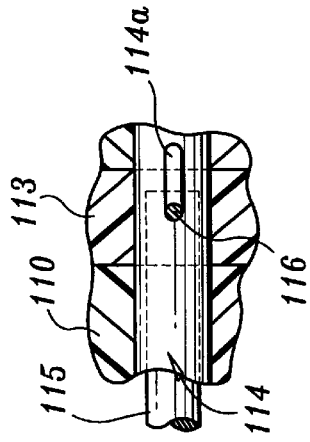
FIG. 4 is a plan view of the connection between the rotating knob and the outer tube and inner shaft taken along line 4—4 in FIG. 2.
Figure 5:
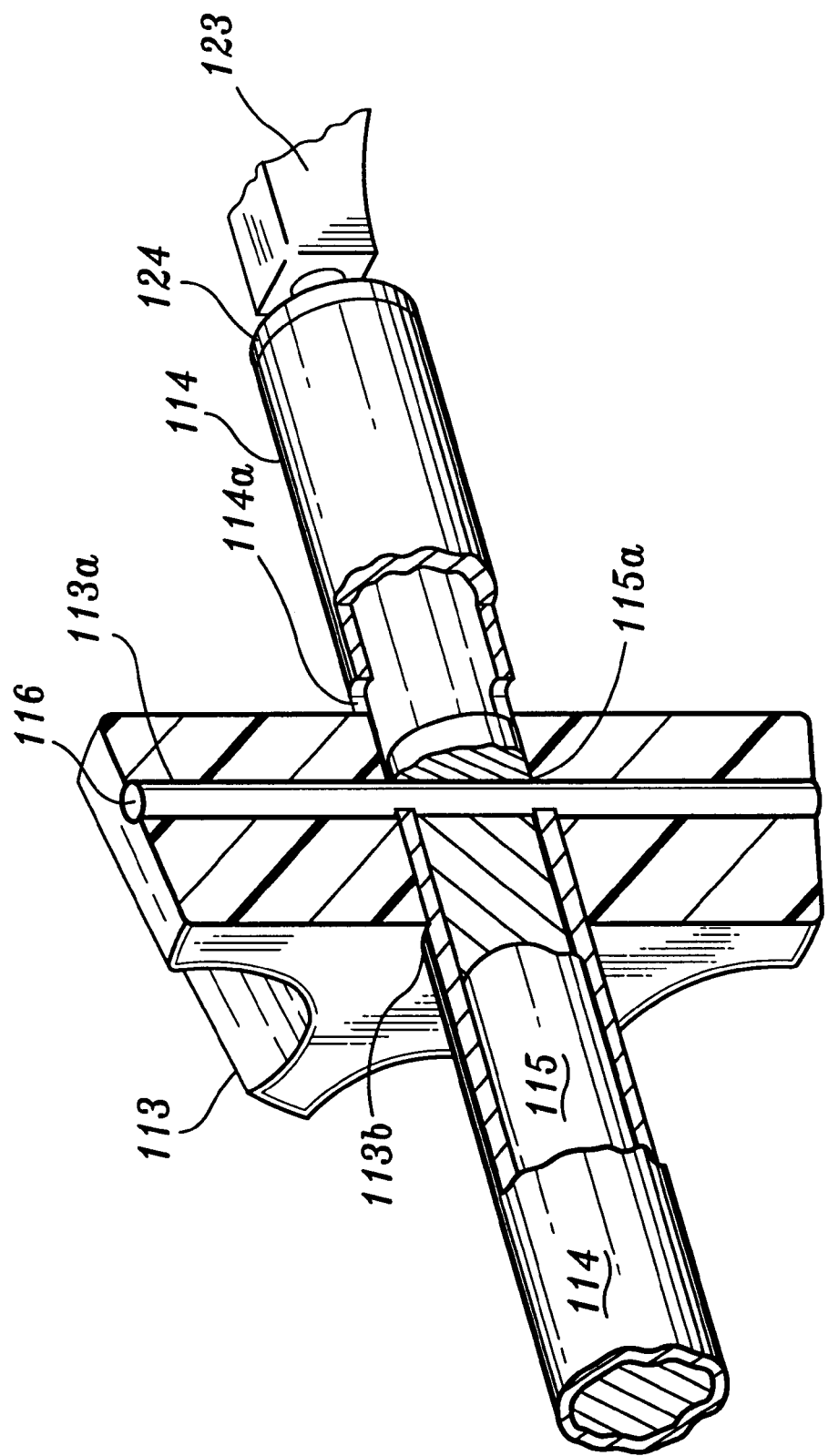
FIG. 5 is a perspective view showing the connection of the rotating knob and the outer tube and inner shaft.

Referring now to FIGS. 2, 4, and 5, knob 113 is rotatably mounted within opening 110b in body 110 and has disposed within it a cross pin 116 extending through aperture 113a of knob 113. Outer tube 114 and shaft 115 are disposed through axial aperture 113b of the knob with cross pin 116 extending laterally through aperture 115a of the shaft and longitudinally oriented elongated slot 114a of the outer tube 114. Elongated slot 114a permits longitudinal motion of outer tube 114 relative to inner shaft 115, as discussed below. As can be seen, when the knob 113 is rotated, both the outer tube 114 and shaft 115 are also rotated.

Figure 3:
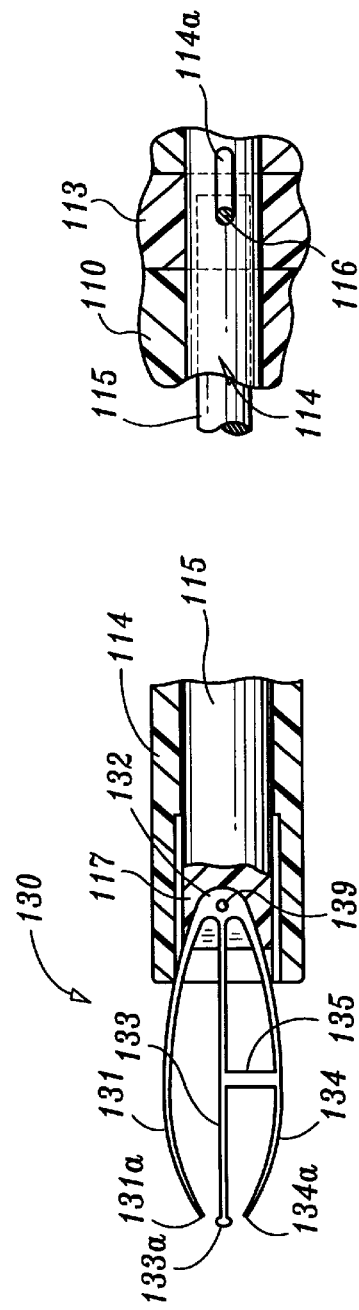
FIG. 3 is a sectional side elevational view of the grasper at the distal end of the apparatus in an unactuated condition.

Referring now to FIG. 3, the grasper 130 is fabricated preferably as a single piece from a resilient plastic or metal, and comprises a pronged structure having a proximal base 132 fixedly attached to distal end portion 117 of shaft 115 by pin 139, and three distal pointing prongs 131, 133, and 134 connected at the base 132. The grasper 130 is also rotated when shaft 115 is rotated.

Prong 131 is arcuate, extending convexly from base 132 such that tip 131a is positioned in the vicinity of the bulbous distal tip 133a of the middle prong 133 but is spaced apart therefrom when grasper 130 is in a relaxed condition.

Middle prong 133 extends longitudinally from base 132 in a rectilinear orientation, and terminates in tissue everting bulbous tip 133a. Tip 133a is preferably spherical but can also be any other shape suitable for the purpose of biasing body tissue into an everted configuration.

Prong 134 is arcuate and extends convexly from base 132 such that tip 134a is positioned in the vicinity of bulbous distal tip 133a but is spaced apart therefrom when the grasper 130 is in a relaxed condition. A strut 135 extends laterally between prongs 133 and 134 at about their midpoints.

It is not desired to have simultaneous closure of tips 131a and 134a with 133a, which would require prior alignment of the blood vessel ends. Rather, sequential closure is preferred to allow the surgeon to first evert and capture one vascular segment end and then evert and capture the second vascular segment end. Sequential closure eliminates the need to hold the blood vessel ends in juxtaposition by other instruments and can be achieved by providing a difference in the force required to close the gaps between prong tips 131a and 133a, and 134a and 133a. Strut 135 provides resistance against flexing of the prongs 133 and 134 towards each other. The amount of resistance can be predetermined by location of the strut 135 closer to or further away from base 132. For example, fabrication of the grasper 130 such that strut 135 is closer to base 132 provides less resistance to closure of tips 133a and 134a.

Figure 6:
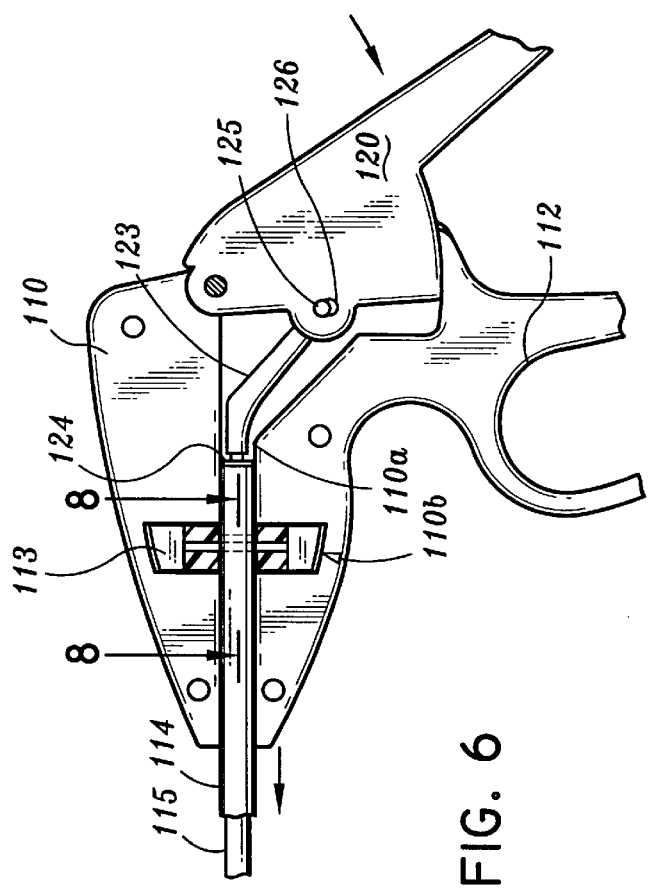
FIG. 6 is a partly sectional cut-away side elevational view of the handle portion in a partly actuated condition.
Figure 8:
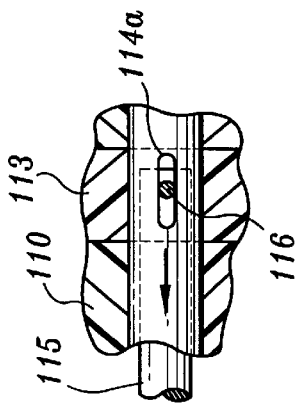
FIG. 8 is a plan sectional view of the connection between the rotating knob and the outer tube and inner shaft in partly actuated condition taken along line 8—8 in FIG. 6.
Figure 7:
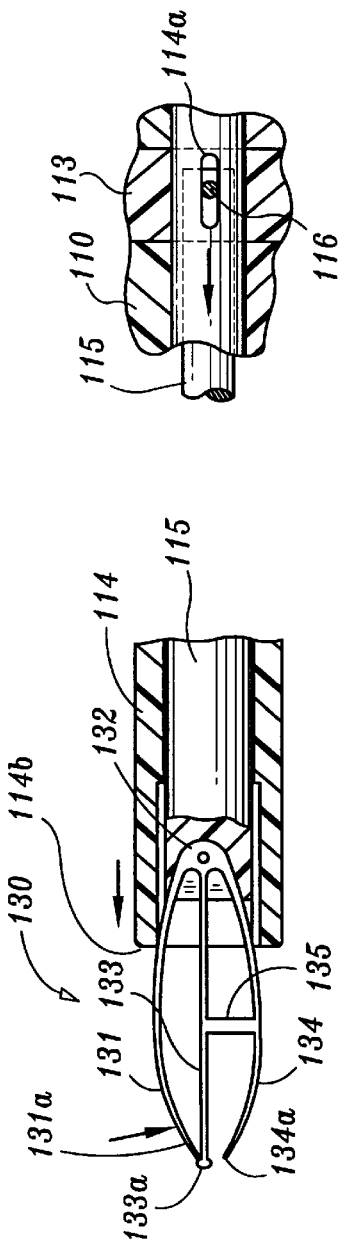
FIG. 7 is a sectional side elevational view of the grasper at the distal end of the apparatus in a partly actuated condition.

Referring now to FIGS. 6, 7, and 8, when trigger 120 is pressed, i.e. moved in the direction of the arrow of FIG. 6, outer tube 114 is urged distally forward. FIG. 8 is illustrates the advancing movement of the outer tube 114 within the body 110. As can be seen, slot 114a allows distal movement of the outer tube 114 relative to the cross pin 116. As outer tube 114 is advanced, annular distal edge 114b (FIG. 7) contacts the outer edges of prongs 131 and 134, and by a camming action, exerts a biasing force which urges the prongs 131 and 134 inwardly toward the middle prong 133. Prong 134 resists such movement, however, because of the buttressing support provided by strut 135. However, prong 131 flexes more readily and tip 131a is moved into contact with bulbous tissue everting tip 133a. In a medical procedure the bulbous tip 133a will have been positioned, for example, in the lumen of a vascular segment. Such positioning causes the edge of the blood vessel to evert. When the gap between tips 131a and 133a is closed, the everted tissue is held between the tips in an everted configuration.

After capturing and everting the end portion of one vascular segment the surgeon proceeds to position the everting tip 133a in the lumen of the second vascular segment to evert the tissue.

Referring now to FIGS. 9, 10, and 11, as the trigger 120 is further pressed and outer tube 114 advances further, the tip 131a exerts further biasing force on tip 133a of the middle prong. The trigger 120 is pressed to fully close the grasper 130, whereupon the everting tip 133a is moved toward tip 134a in response to the biasing action of tip 131a as shown in FIG. 10. The gap between tips 133a and 134a is closed, thereby providing for capture of tissue 400 held therebetween. As seen in FIG. 11 the slot 114a is fully advanced relative to cross pin 116, which abuts the proximal end of the slot to prevent further distal movement of the outer tube 114. Thus, at full closure of apparatus 100 during an operation, the end portions of two blood vessels segments are held in close alignment with the tissue everted to form a flange-like structure.

It is also contemplated that a positive stop can be incorporated in the apparatus to provide a two step closure, i.e. to first approximate tip 131a and tip 133a followed by a distinct step of approximating tip 133a and tip 134a. The apparatus can include some type of indicator to indicate to the user when the first step (approximation of tip 131a and tip 133a) is completed.

After eversion of the tissue, next, a clip or other type fastener can be applied to the everted tissue, to effect fixation of the vessel ends in the joined configuration. Complete joining of the blood vessel ends may require placement of several clips. Clips such as those described in U.S. application Ser. No. 08/527,698 filed Sep. 13, 1995 and European Publication No. 0656191 published on Sep. 20, 1995 and herein incorporated by reference are preferably applied (using the applied disclosed in that application) to the everted portion of the tissue. The clips themselves are non-penetrating and hold the tissue with minimal trauma to the area of tissue joined by healing.

Figure 12:
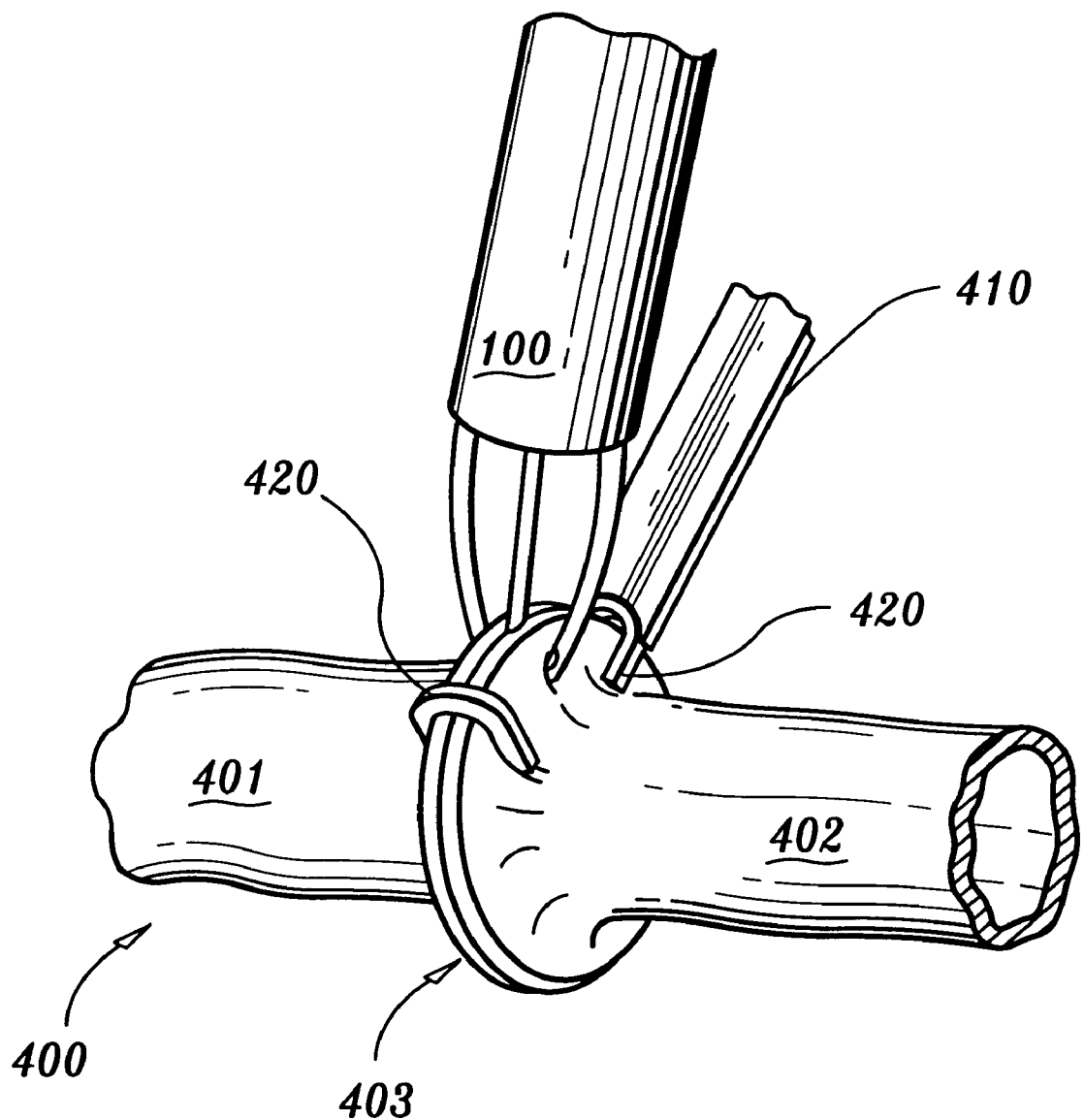
FIG. 12 is a perspective view illustrating the joining of vascular segments.

Referring to FIG. 12, eversion of body tissue is illustrated wherein a blood vessel 400, divided into vascular segments 401 and 402, is joined by tissue everting apparatus 100 to form a flange like structure 403 of everted tissue at the respective end portions of the vascular segments 401, 402. The inner surfaces of the vascular segments are joined in close contact at the flange structure 403. A clip applier 410 (shown schematically) is then used to apply a series of clips 420 to the flange like structure 403 to hold the end portions together. A sufficient number of clips is applied to secure sealing of the tissue. After a period of time the internal surfaces of the tissue joined at the flange like structure 403 heal together to form a juncture of tissue. The clips, if bioabsorbable, will eventually degrade and dissolve into the body.

Figure 13:
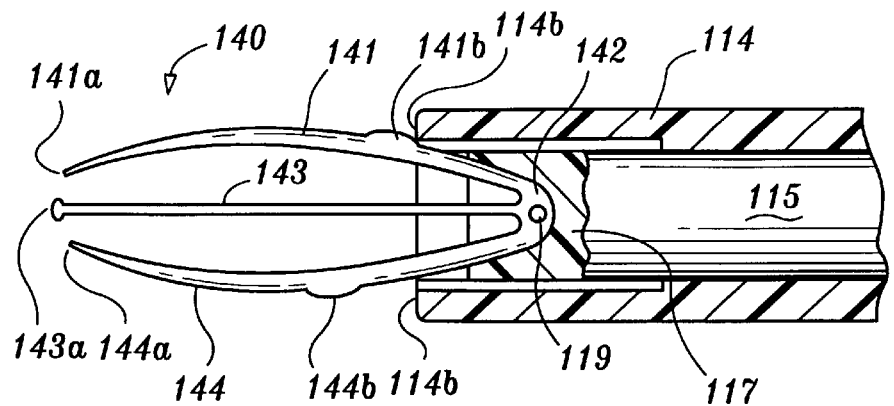
FIGS. 13, 14, and 15, are partly sectional side elevational views sequentially illustrating a second embodiment of the grasper in initial, intermediate, and fully actuated conditions.
Figure 14:
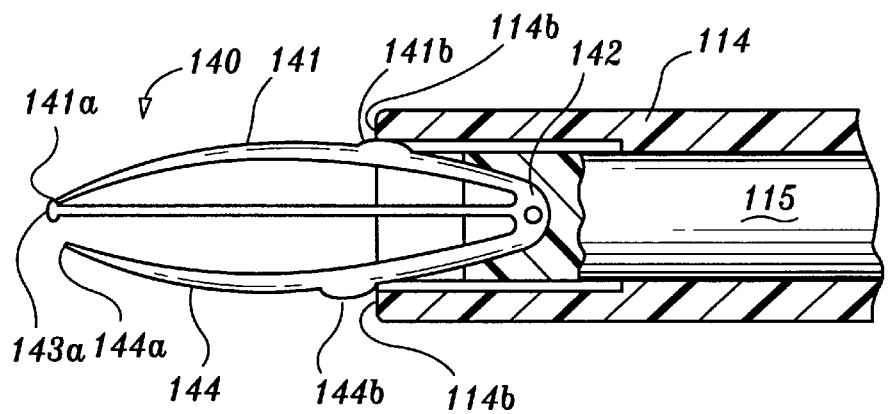
Figure 15:
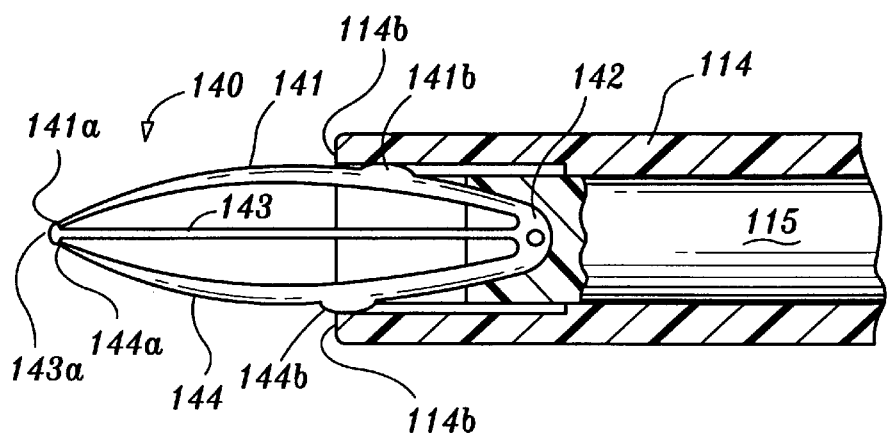

Referring now to FIGS. 13, 14, and 15, an alternative embodiment of the grasper is shown wherein sequential closure of the prongs is achieved by sequential camming action. The instrument is otherwise the same as described above.

Grasper 140 comprises a first outer prong 141, a middle prong 143, and a second outer prong 144, all joined at base 142, which is connected to the distal end 117 of shaft 115 by pin 119. First outer prong 141 is convexly curved and includes distal tip 141a and a camming projection 141b. Middle prong 143 is rectilinear and includes a tissue everting bulbous tip 143a. Second outer prong 144 is convexly curved and includes a distal tip 144a and a camming projection 144b. There is no strut between the middle prong 143 and outer prong 144. As can be seen camming projection 141b is positioned closer to base 142 than is camming projection 144b. Thus, as the outer tube 114 moves distally, annular distal edge 114b first contacts camming projection 141b, thereby closing the gap between tips 141a and 143a. (See FIG. 14) As the outer tube 114 is moved further, distal edge 114b thereafter contacts camming projection 144b, thereby closing the gap between tips 144a and 143a. (See FIG. 15) Unlike the previously described grasper embodiment 130, outer prong 144 is moved towards the middle prong 143, which remains stationary.

A tactile indicator can be provided to inform the user that the first step, i.e. camming of prong tip 141a towards bulbous tip 143a, has been completed.

Figure 16:
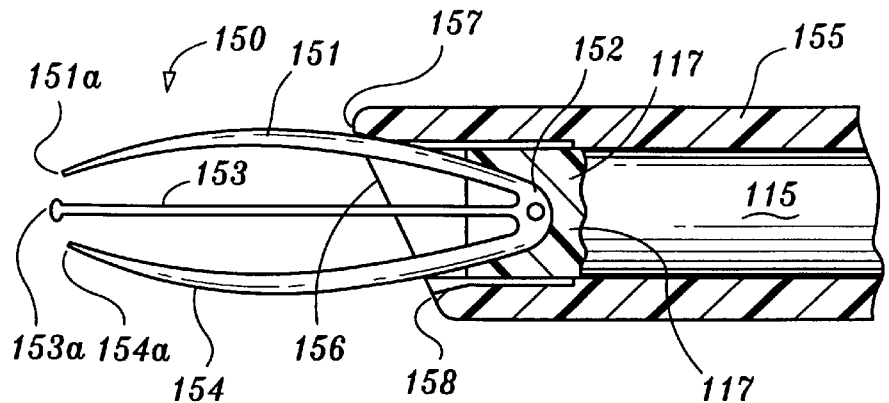
FIGS. 16, 17, and 18 are partly sectional side elevational views sequentially illustrating a third alternative embodiment of the grasper and outer tube in initial, intermediate and fully actuated stages of operation.
Figure 17:
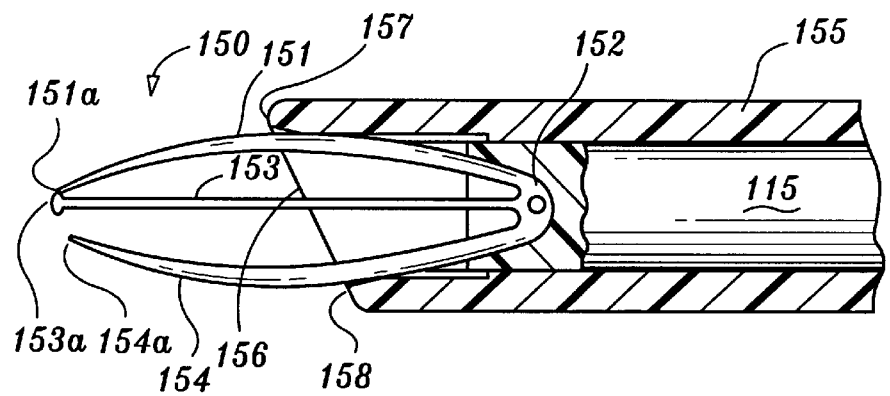
Figure 18:
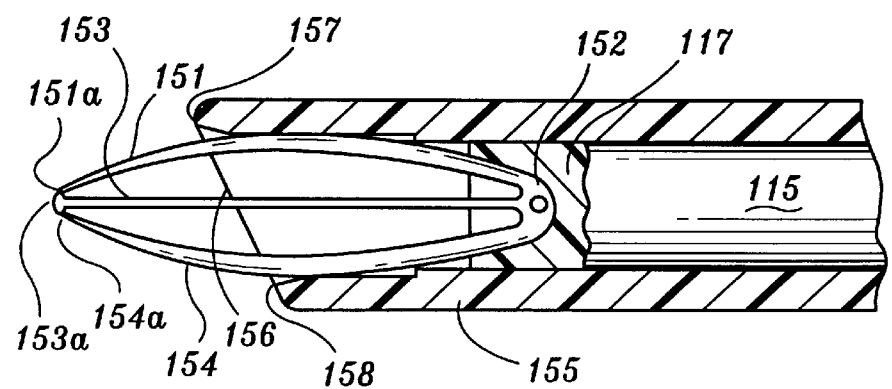

In yet another embodiment shown in FIGS. 16, 17, and 18, the grasper 150 includes three prongs 151, 153, 154 corresponding to prongs 141, 143, and 144, respectively, except that there are no corresponding camming projections. Base 152 of the grasper 150 is fixedly connected to the distal end portion 117 of the shaft 115. Grasper 150 is substantially laterally symmetrical. Sequential closure of the prongs of grasper 150 are achieved by an outer tube 155 which has a bevelled end 156 such that distally further edge 157 contacts the outer edge of prong 151 before the opposite edge 158 contacts the outer surface of prong 154. Accordingly, as the outer tube 155 is advanced, tip 151a of prong 151 will be biased toward everting tip 153a of prong 153 prior to the biasing of tip 154a toward everting tip 153a.

The embodiments of FIGS. 1–18 are designed for minimally invasive procedures. Due to their remote actuation and elongated outer tube, they can be inserted through a trocar cannula (not shown) to evert the tissue under vision in endoscopic procedures.

Figure 19:
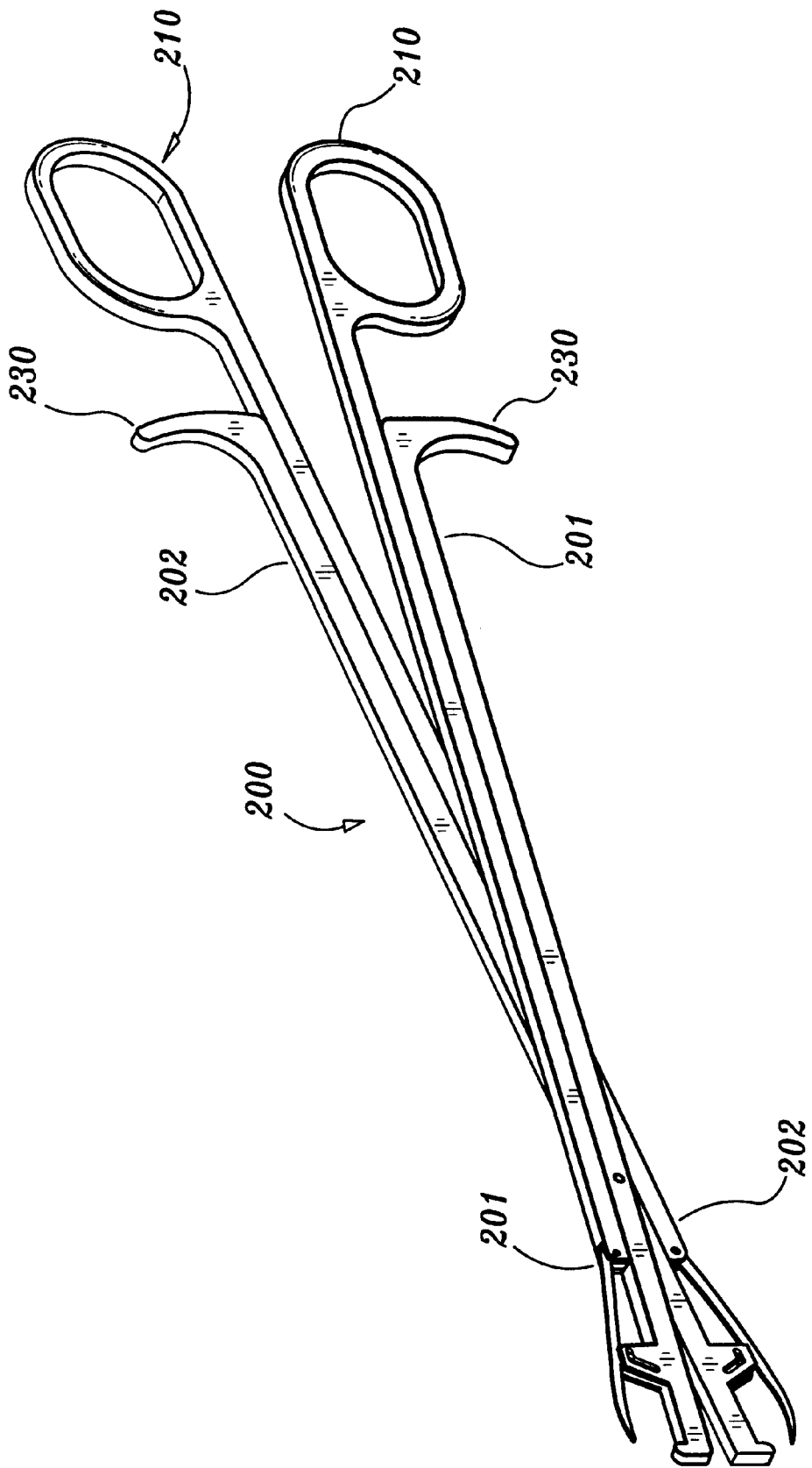
FIG. 19 is a perspective view of a fourth alternative embodiment of a tissue everting apparatus.
Figure 20:
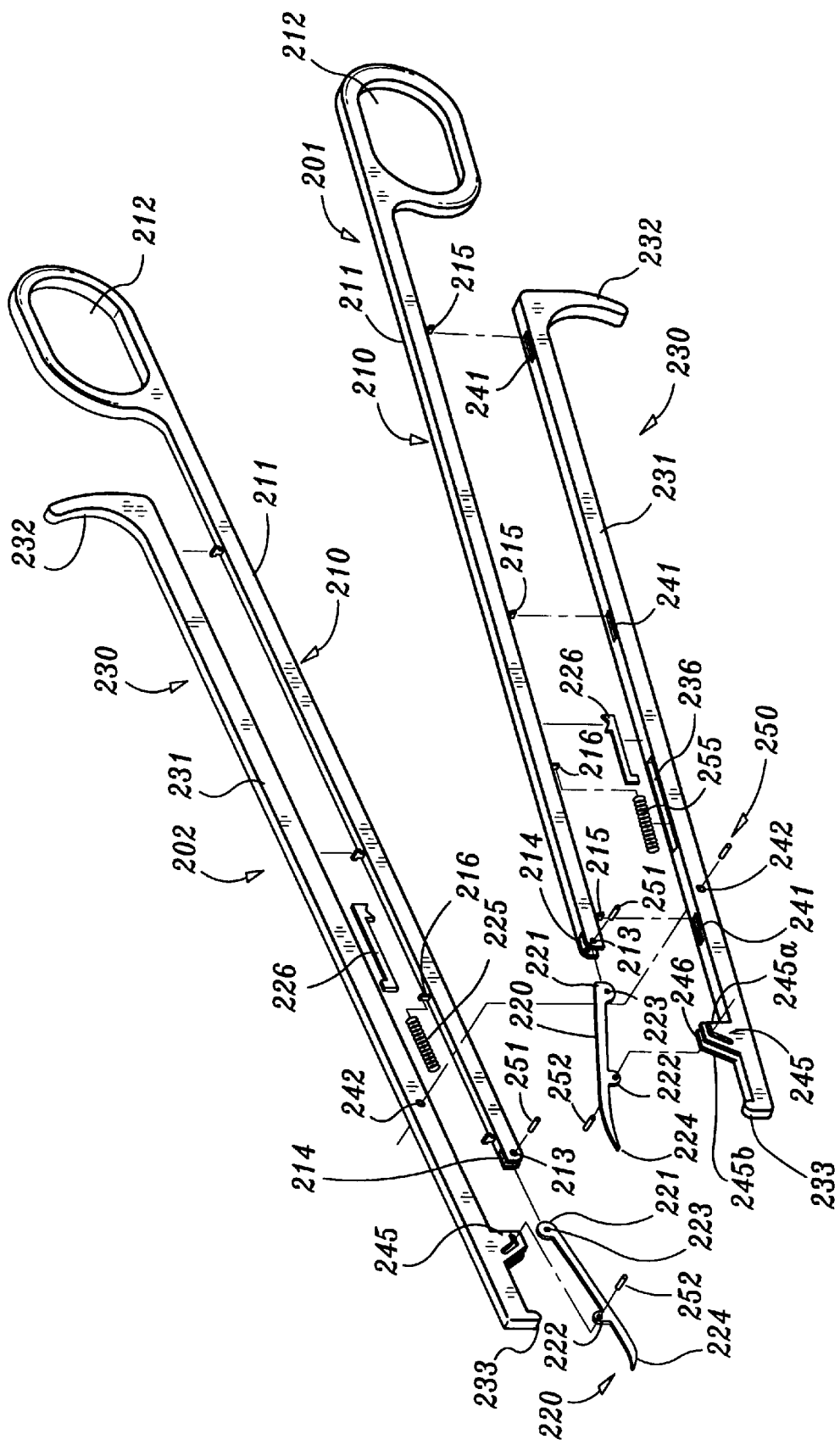
FIG. 20 is an exploded perspective view of the apparatus of FIG. 19.

Referring now to FIGS. 19, 20, and 22, an alternative, non-endoscopic embodiment of the tissue everting apparatus is shown. Tissue everting forceps 200 includes first and second tissue everting and holding mechanisms 201 and 202, respectively. The first and second tissue everting and holding mechanisms 201 and 202 are pivotally attached to each other and oriented for everting and holding opposing tissue end portions.

Each tissue everting and holding mechanism 201, 202 includes an actuator 210 slidably attached to an arm 230.

More particularly each actuator 210 includes a lengthwise oriented elongated portion 211 with a finger catch (i.e. ring 212) at its proximal end. At its distal end lengthwise portion 211 includes a slot 214 with transverse aperture 213. Slot 214 receives the proximal end portion 221 of jaw 220. Pin 251 is disposed through transverse aperture 213 in elongated portion 211 and through aperture 223 in proximal end portion 221 of the jaw.

Jaw 220 is an elongated member also having a distal tissue grasping tip 224 and an aperture 222 through which cam follower pin 252 is laterally disposed.

At least one and preferably three T-shaped projections 215 extend from elongated portion 211 and are adapted to engage respective corresponding slots 241 in arm 230. (See FIG. 23)

Backstop 216 extends from elongated portion 211 and provides a stop surface for retaining helical compression spring 225 within slot 236 in arm 230. Compression spring 225 is positioned between proximally facing wall 237 and backstop 216, and biases the actuator to a proximal position.

A leaf spring 226 is fixedly attached within slot 217 of actuator 210 and extends longitudinally within slot 236. Spring 226 includes a base 227 which is mounted in slot 217, an elongated mid portion 228, and a tip 229 which cams against the sides of baffle 238.

Arm 230 includes an elongated portion 231, a proximal finger rest 232, and a distal everting tip 233. Each arm 230 includes lateral aperture 242. Pivot pin 250 extends through the aperture 242 of each arm to pivotally join the arms. The first and second tissue everting and holding mechanisms 201 and 202 are oriented such that the actuators 210 are on opposite top and bottom (as shown) sides of the forceps 200.

Figure 21:
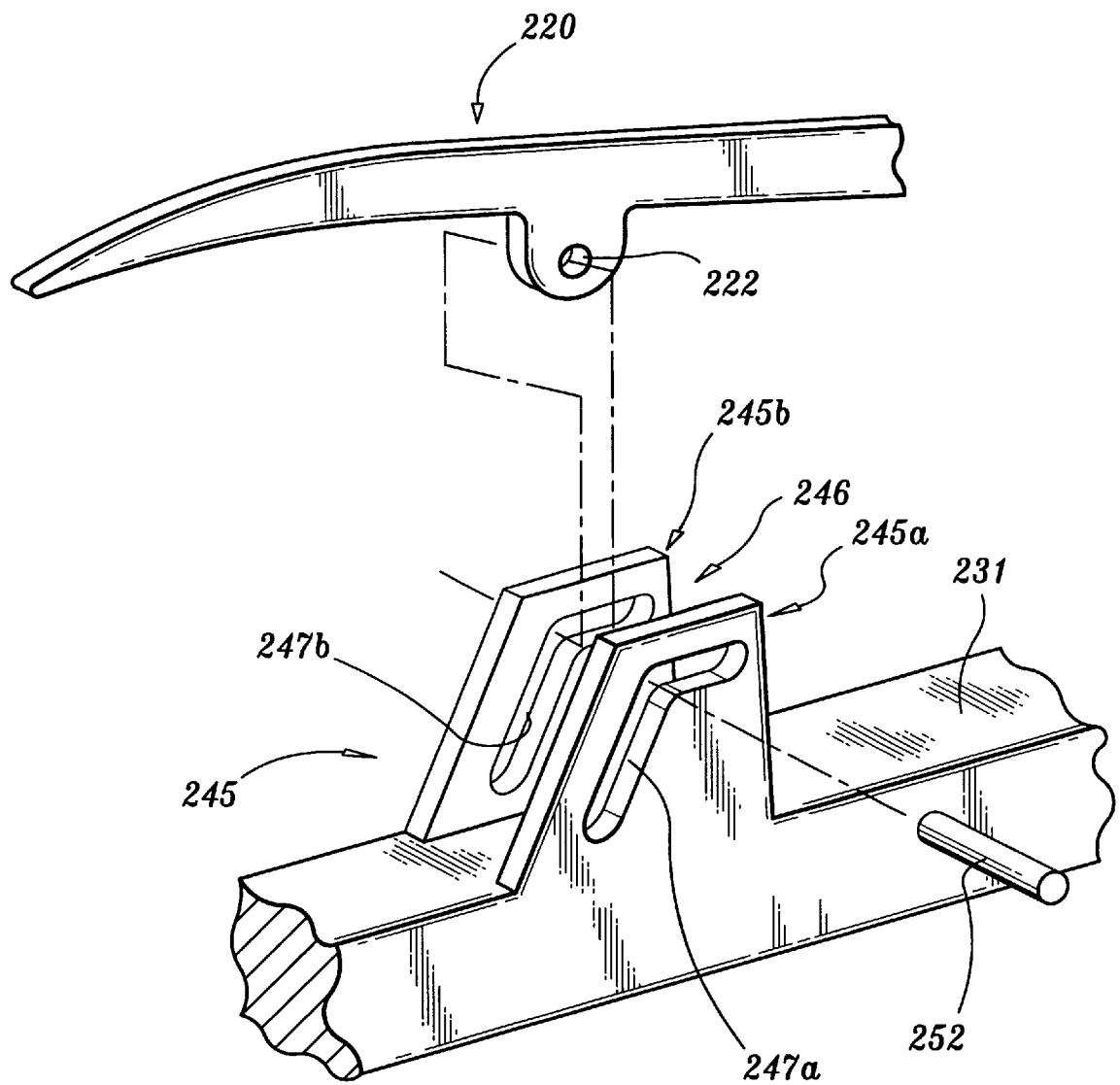
FIG. 21 is an exploded perspective view showing the camming linkage between the jaw and arm of the embodiment of FIG. 19.

Referring to FIG. 21, projection 245 extends laterally from the elongated portion 231 and includes two spaced apart walls 245a and 245b which define a slot 246 between them which is adapted to receive the jaw 220. Each wall 245a and 245b includes a respective camming slot 247a and 247b. Cam follower pin 252 is disposed through slots 247a and 247b, as well as through aperture 222 in the jaw.

Referring now to FIGS. 22, and 24–26, baffle 238 extends from the floor of slot 236 and includes a proximally pointing rounded narrow tip 238a and a relatively wider distal back portion 238b with a notch 238c.

Referring to FIGS. 24, 25, and 26 baffle 238 is oriented at an angle from the longitudinal axis of the arm 230 such that when leaf spring 226 is advanced by distally moving actuator 210 the tip 229 contacts one side 238d of the baffle and is laterally biased to one side. upon reaching the back 238b of the baffle the camming tip 229 is moved into notch 238c where it rests, as shown in FIG. 26. The actuator is thereby locked into position. However, at this position the actuator is not at its most distal position and can be advanced a little further. As can be seen in FIGS. 27 and 28, when the jaws are closed, pins 252 have not yet reached the distal ends of slots 247a and 247b. The remaining clearance between pins 252 and the distal ends of slots 247a and 247b permits further advancement of actuators 210 to release the actuators from the locked position. As can be seen from FIGS. 30, 31, 32, when the leaf spring tip 229 is distally advanced out of notch 238c of the baffle 238, it resiliently shifts laterally, then cams against side 238e of the baffle The lateral shifting of tip 229 unlocks the leaf spring 226 and permits withdrawal of the respective actuator 210 to its initial open-jaw position.

The forceps 200 embodies two types of actions: a scissor-like pivoting motion between first and second tissue everting and holding mechanisms 201, 202 around pivot pin 250, and the opening and closing action of jaws 220 individually actuated by the linear movement of actuators 210.

Referring to FIGS. 27–34 the operation of the forceps 200 is shown. First, the everting tip 233 of the first tissue everting and holding mechanism 201 is positioned in the lumen of the end portion of vascular segment 401 to evert the end portion. Actuator 210 is advanced distally, thereby also moving the jaw 220. Cam follower pin 252, being disposed through L-shaped slots 247a and 247b, is cammed toward the center of the forceps 200, thereby causing the jaw 220 to pivot at pin 251 and close upon the everted vascular end portion 401 to hold it in a flange like structure, as can be seen in FIG. 27.

As shown in FIG. 28, the same operation is performed with the second tissue everting and holding mechanism 202 to capture the end portion of the second vascular segment 402.

Next, as shown in FIG. 29, the first and second tissue everting and holding mechanisms 201 and 202 are pivoted closed by the scissors-like action in order to bring the everted vascular end segments together in close appositions. The jaws 220 are held closed by the leaf spring 226, the tip 229 which is retained by notch 239 of the baffle, thereby preventing the proximal return of the actuator 210. The everted body tissue can then be fastened by the application of surgical clips as discussed above.

Referring now to FIGS. 33-34, to open the jaws 220 to release the body tissue, each actuator 210 is advanced a little bit further to distal-most position. As mentioned above, this action moves the tip 229 of the leaf spring out of notch 239 of the baffle. See FIGS. 30 and 31. The actuator 210 is then proximally moved by the biasing force of compression spring 225 back to its initial most proximal position. The jaws 220 of both first and second tissue everting and holding mechanisms 201 and 202 are returned to the open position and then the forceps can be withdrawn from the operating site.

While the above description contains many specifics, these specifics should not be construed as limitations on the scope of the invention, but merely as exemplifications of preferred embodiments thereof. For example, the endoscopic everting instrument 100 can also be used in open procedures. Various materials of construction and size dimensions can be chosen which are suitable for the use described herein. Those skilled in the art will envision many other possible variations that are within the scope and spirit of the invention as defined by the claims appended hereto.

What is claimed is:

1. An apparatus for everting body tissue, which comprises:

a) a handle portion;

b) an endoscopic portion extending from the handle portion, the endoscopic portion including an actuator longitudinally movable between a first position and a second position;

c) a tissue everting tip extending distally from the endoscopic portion;

d) first and second prongs extending distally from the endoscopic portion and being relatively movable with respect to each other in at least a partly lateral direction between a laterally open position and a closed tissue-capturing position in response to the longitudinal movement of the actuator between first and second positions; and e) a third prong positioned between the first and second prongs and terminating in the tissue everting tip, the first, second and third prongs being connected at a proximal base portion, the proximal base portion being fixedly connected to a distal end of the endoscopic portion, the first, second and third prongs and the base portion forming a grasper.

2. The apparatus of claim 1 wherein the actuator comprises a tubular member configured to cam at least one of the prongs.

3. An apparatus for everting body tissue, which comprises:
   a) a handle portion;
   b) an endoscopic portion extending from the handle portion, the endoscopic portion including an actuator longitudinally movable between a first position and a second position;
   c) a tissue everting tip extending distally from the endoscopic portion; and
   d) first and second prongs extending distally from the endoscopic portion and being relatively movable with respect to each other in at least a partially lateral direction between a laterally open position and a closed tissue-capturing position in response to the longitudinal movement of the actuator between the first and second positions; and
   e) a third prong positioned between the first and second prongs and terminating in the tissue everting tip, the first, second, and third prongs being connected at a proximal base portion, the proximal base portion being fixedly connected to a distal end of the endoscopic portion, the first, second, and third prongs and the base portion forming a grasper,
   wherein the second prong is connected to the third prong by a laterally extending reinforcement strip spaced from the base, the third prong extending distally and rectilinearly from the base and the first and second prongs extending arcuately from the base.

4. The apparatus of claim 1 wherein the tissue everting tip of the third prong is a bulbous portion positioned at the distal end, the third prong being biased to a distal end of the second prong in response to movement of the actuator from the first position to the second position and after movement of the first prong to the closed tissue-capturing position.

5. The apparatus of claim 1 wherein the tissue everting tip of the third prong is a bulbous portion positioned at the distal end, and distal ends of the first and second prongs are biased toward the tissue everting tip in response to movement of the actuator from the first position to the second position.

6. The apparatus of claim 5 wherein the movement of the actuator from the first position to the second position is linear movement in a distal direction.

7. The apparatus of claim 6 wherein the distal ends of the first and second prongs are sequentially biased in response to contact by a distal edge of the actuator.

8. The apparatus of claim 7 wherein the first and second prongs each having a convex camming projection on an exterior surface, the convex camming projections being unequally spaced from the base of the grasper, the camming projections being sequentially contacted by the distal edge of the actuator.

9. An apparatus for everting body tissue, which comprises:
   a) a handle portion;
   b) an endoscopic portion extending from the handle portion, the endoscopic portion including an actuator longitudinally movable between a first position and a second position;
   c) a tissue everting tip extending distally from the endoscopic portion;
   d) first and second prongs extending distally from the endoscopic portion and being relatively movable with respect to each other in at least a partially lateral direction between a laterally open position and a closed tissue-capturing position in response to the longitudinal movement of the actuator between the first and second positions; and
   e) a third prong positioned between the first and second prongs and terminating in the tissue everting tip, the first, second, and third prongs being connected at a proximal base portion, the proximal base portion being fixedly connected to a distal end of the endoscopic portion, the first, second, and third prongs and the base portion forming a grasper,
   wherein the tissue everting tip of the third prong is a bulbous portion positioned at a distal end of the third prong, and distal ends of the first and second prongs are sequentially biased toward the tissue everting tip in response to distal movement of the actuator from the first position to the second position and contact by a distal edge of the actuator,
   wherein the distal edge of the actuator is angled so as to contact one of the first and second prongs before contacting the other of the first and second prongs.

10. A method for everting and fastening two segments of body tissue, comprising:
    a) providing a tissue everting instrument which includes
       i) at least one elongated frame defining a longitudinal axis,
       ii) at least one actuator slidably mounted to the at least one frame and longitudinally movable between a proximal first position and a distal second position,
       iii) at least one tissue everting tip, and
       iv) at least first and second prongs, each prong being movable in at least a partly lateral direction between a laterally open position and a closed tissue-capturing position in response to the longitudinal movement of the actuator between first and second positions;
    b) positioning the tissue everting tip adjacent an edge of a first segment of body tissue to evert and position the edge of the first segment between the tissue everting tip and an end portion of the first prong;
    c) moving the first prong from the laterally open position to the closed tissue-capturing position;
    d) positioning the tissue everting tip adjacent an edge of a second segment of body tissue to evert and position the edge of the second segment between the tissue everting tip and an end portion of the second prong; and
    e) moving the second prong from the laterally open position to the closed tissue-capturing position.

11. The method of claim 10 further comprising the step of applying at least one surgical clip to the everted edges of the first and second segments of body tissue to fasten the edges together.

* * * * *